United States Patent [19]

Howell

[11] Patent Number: 4,820,497
[45] Date of Patent: Apr. 11, 1989

[54] MOVABLE CLEANING ASSEMBLY FOR AN ASPIRATING NEEDLE

[75] Inventor: Gary W. Howell, Newark, Del.
[73] Assignee: E. I. Du Pont de Nemours and Company, Wilmington, Del.
[21] Appl. No.: 877,635
[22] Filed: Jun. 23, 1986
[51] Int. Cl.$^4$ .............................. G01N 35/00
[52] U.S. Cl. .................. 422/63; 73/864.81; 134/198; 422/100; 436/49
[58] Field of Search .................. 73/864.81; 134/198–200; 422/63–67, 100; 436/49

[56] References Cited

U.S. PATENT DOCUMENTS

| | | | |
|---|---|---|---|
| 2,009,078 | 7/1935 | Ziska | 148/20 |
| 2,565,855 | 8/1951 | Jordan | 134/64 |
| 3,044,098 | 7/1962 | Stalson | 15/302 |
| 3,081,158 | 3/1963 | Winter | 23/253 |
| 3,143,393 | 6/1960 | De Sequin | 23/253 |
| 3,192,968 | 7/1965 | Baruch et al. | 141/82 |
| 3,193,359 | 7/1965 | Baruch et al. | 23/259 |
| 3,197,285 | 7/1965 | Rosen | 23/253 |
| 3,241,923 | 3/1966 | Ferrar | 23/259 |
| 3,252,330 | 5/1966 | Kling | 422/64 X |
| 3,266,322 | 8/1966 | Negersmith | 73/423 |
| 3,430,495 | 3/1980 | Burge | 73/423 |
| 3,475,130 | 10/1969 | Baruch | 23/253 |
| 3,481,709 | 12/1969 | Slone | 23/253 |
| 3,551,112 | 12/1970 | Sequeira et al. | 23/259 |
| 3,552,212 | 1/1971 | Oblin | 73/423 |
| 3,609,040 | 9/1971 | Kuzel | 356/36 |
| 3,687,632 | 8/1972 | Natelson | 23/259 |
| 3,716,338 | 2/1973 | Moran | 23/259 |
| 3,764,041 | 9/1973 | Noll | 222/1 |
| 3,826,621 | 7/1974 | Johnson, Jr. et al. | 23/259 |
| 3,842,680 | 10/1974 | Vollick et al. | 73/425.4 P |
| 3,858,450 | 7/1975 | Jones | 73/423 A |
| 3,900,289 | 8/1975 | Liston | 23/230 R |
| 3,912,456 | 10/1975 | Young | 23/253 |
| 3,964,526 | 6/1976 | Sindermann | 141/1 R |
| 4,000,973 | 1/1977 | Petersen | 23/230 R |
| 4,000,974 | 1/1977 | Acord | 23/230 R |
| 4,054,415 | 10/1977 | Seligson | 23/253 R |
| 4,076,503 | 2/1978 | Atwood et al. | 23/259 |
| 4,108,602 | 8/1978 | Hanson | 23/230 R |
| 4,217,780 | 8/1980 | O'Connell | 73/421 R |
| 4,245,509 | 1/1981 | Mody | 73/423 A |
| 4,252,769 | 2/1981 | Hood et al. | 422/50 |
| 4,318,885 | 3/1982 | Suzuki et al. | 422/68 |
| 4,323,537 | 4/1982 | Mody | 422/63 |
| 4,469,526 | 9/1984 | Budinsky et al. | 134/200 X |

OTHER PUBLICATIONS

Finley, Paul R. et al., "Evaluation of A New Multichannel Analyzer, 'Astra 8'", Clinical Chemistry, vol. 24, No. 12, (1978), pp. 2125–2131.

*Primary Examiner*—Michael S. Marcus

[57] ABSTRACT

A liquid dispensing apparatus is characterized by a cleaning arrangement movable with the aspirating needle of the apparatus. The cleaning arrangement includes a pair of mating wellheads one of which has a flange with a planar surface thereon. The other of the wellheads has a corresponding cutout therein. When registered, the wellheads cooperate to define a well-like chamber with a closed bottom. The wellheads are each mounted on an arm which is movable from open to closed dispositions in response to movement of the aspirating needle.

29 Claims, 6 Drawing Sheets

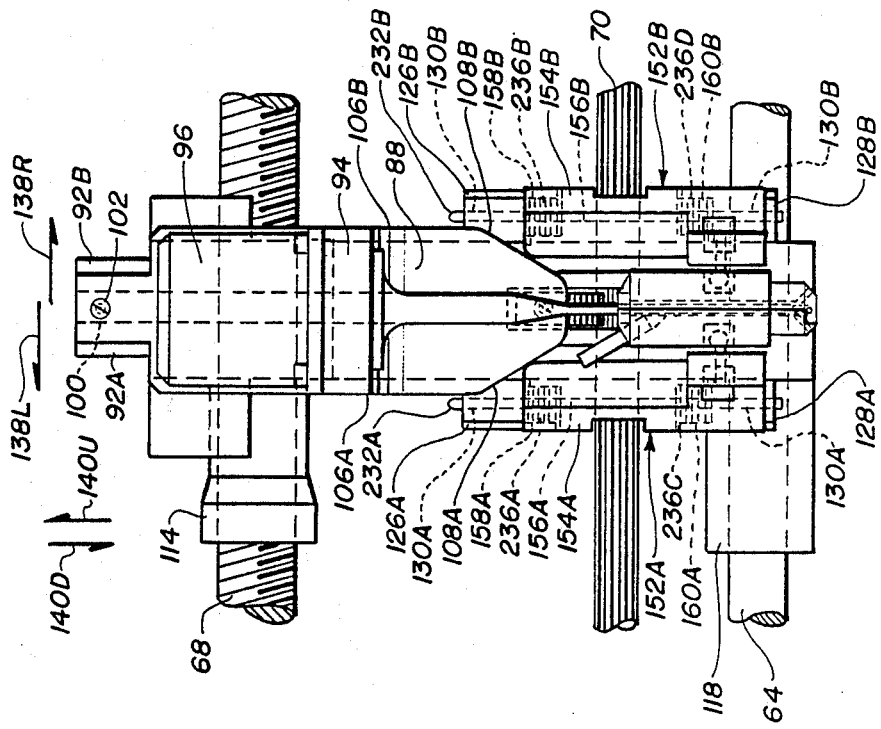
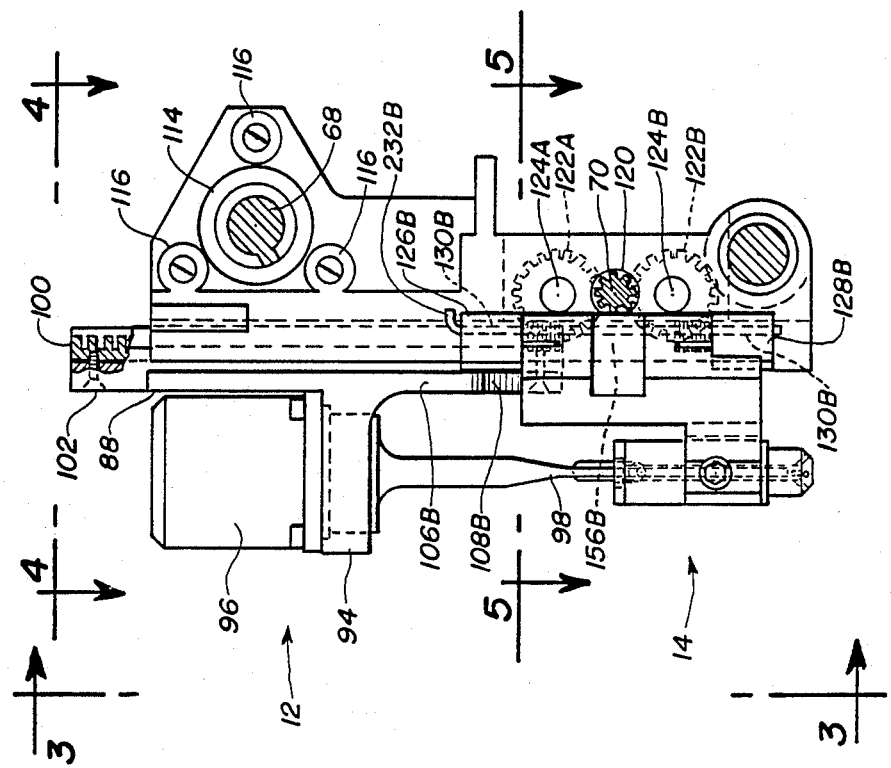
Fig. 3
Fig. 2

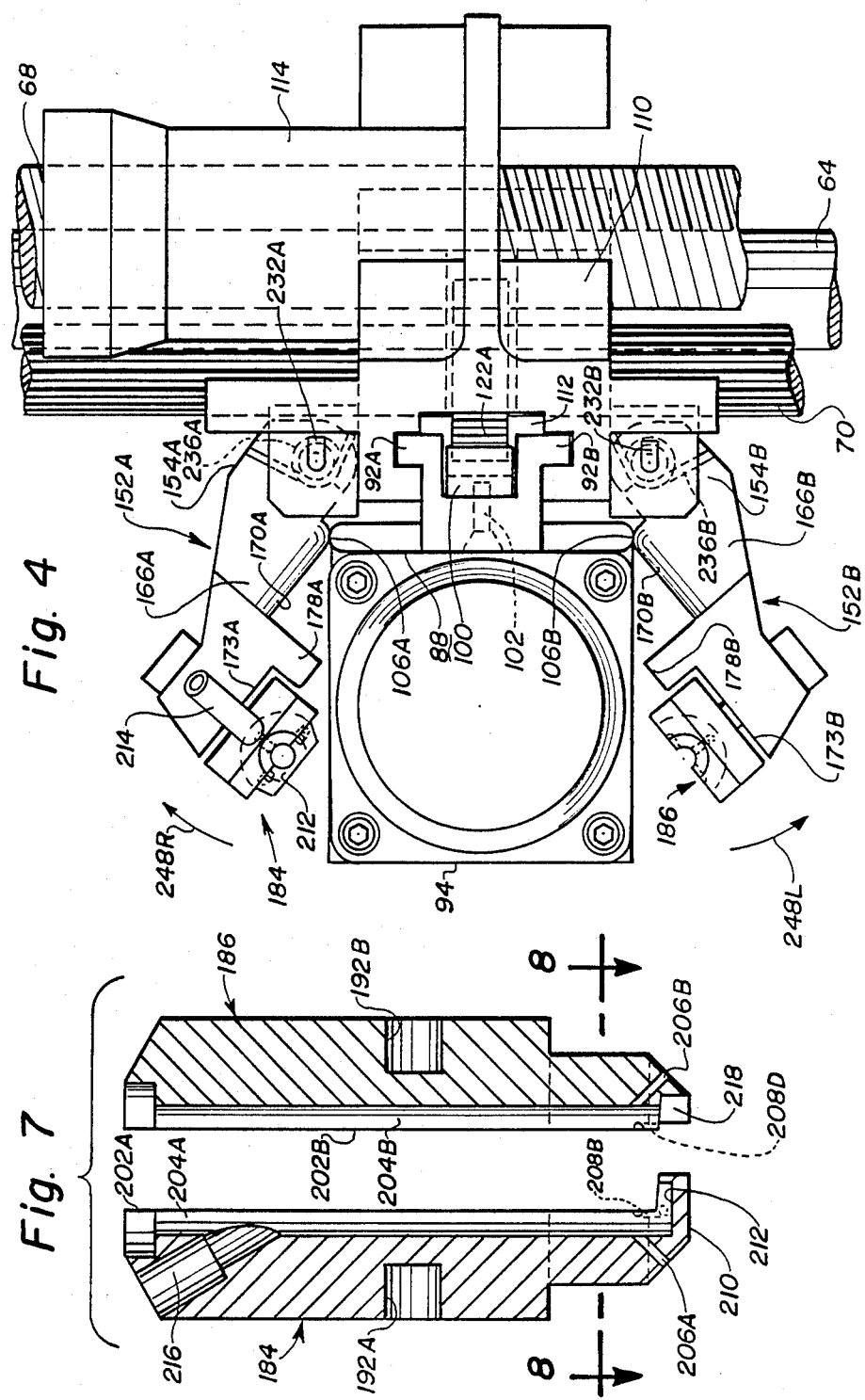

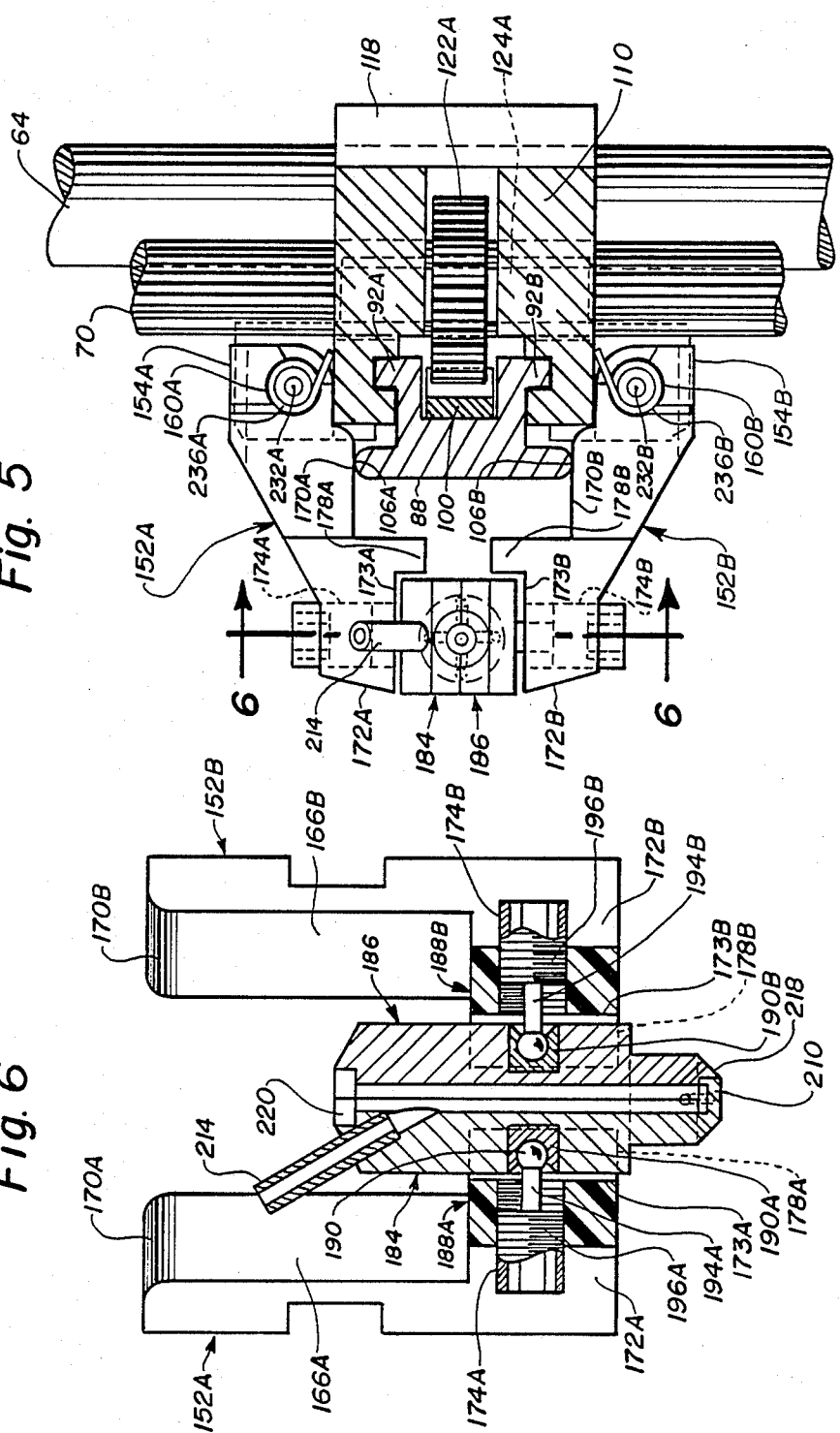

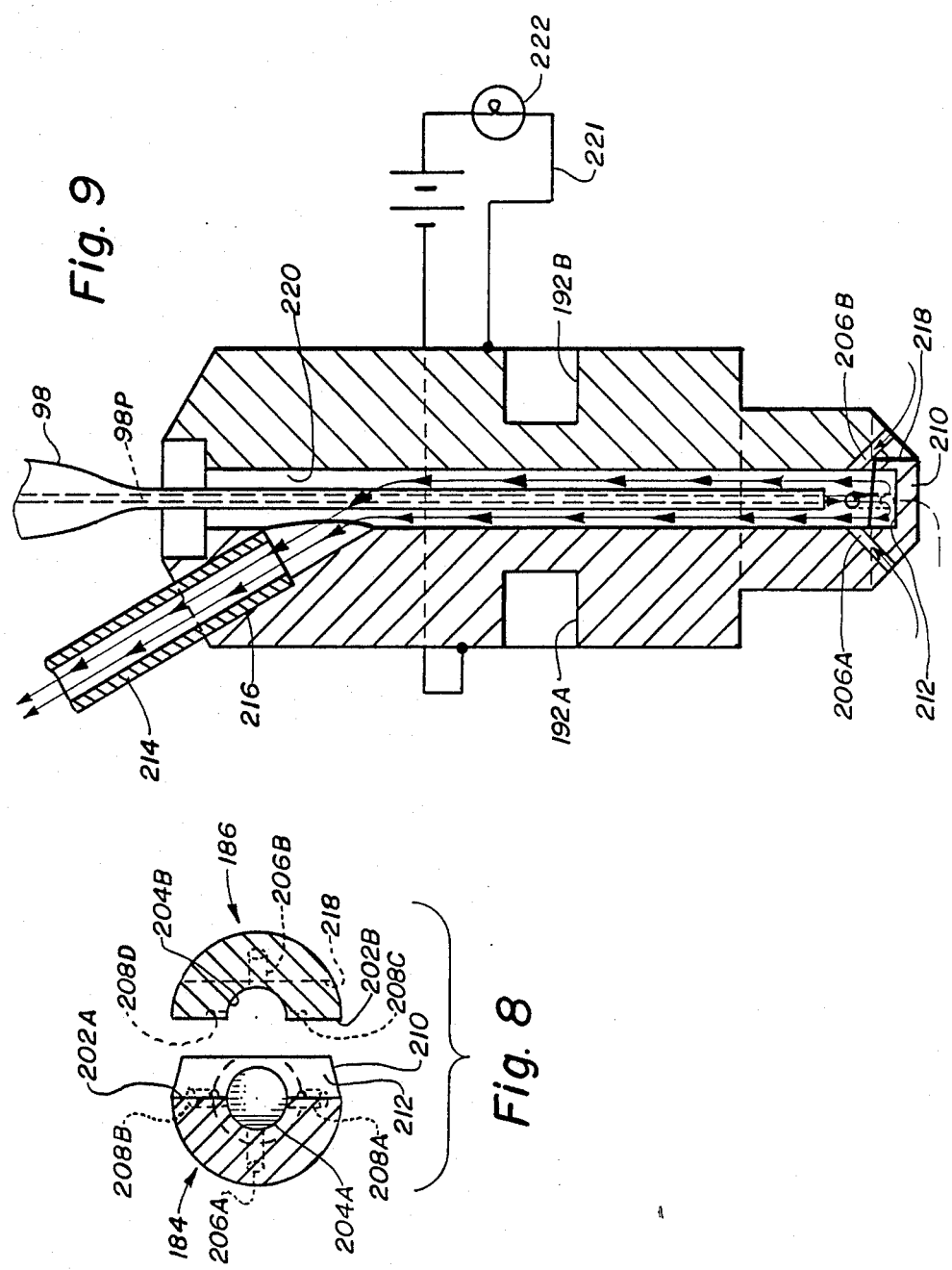

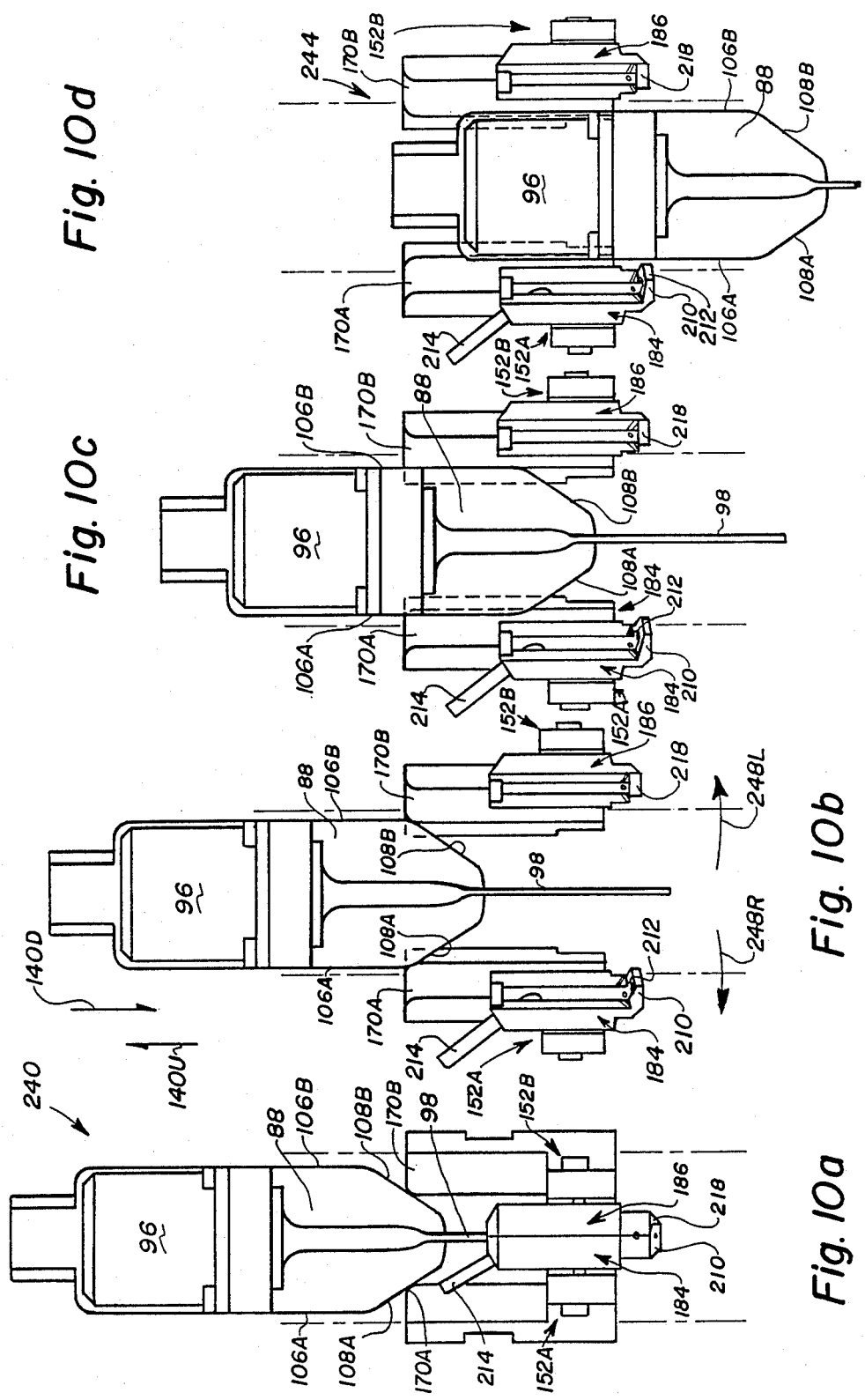

MOVABLE CLEANING ASSEMBLY FOR AN ASPIRATING NEEDLE

BACKGROUND OF THE INVENTION

1. Field of the Invention

The present invention relates to a chemical analysis instrument having an aspirating needle and, in particular, to an analysis instrument having a movable cleaning assembly for cleaning the aspirating needle.

2. Description of The Prior Art

Most apparatus operative to perform automated chemical analysis of liquid samples use an aspirating probe, or needle, to transfer predetermined volumes of liquid sample or liquid reagent between receptacles disposed at various locations on the instrument. The aspirating probe is typically an elongated, needle-like member having a hollow passage whereby liquid may be drawn into and dispensed from the probe.

A common problem in such aspirating needle arrangements is the risk of liquid "carryover". Carryover is usually manifested as the contamination of a given reagent supply or a given sample volume by the introduction thereinto of other reagents or samples. Carryover occurs when a needle having residual traces of a previously dispensed sample or reagent is introduced into volume of a different reagent or sample.

Carryover has an additional deleterious aspect in that it may result in the introduction of an inaccurate amount of sample or reagent. The presence of additional unwanted droplets of sample or reagent on the exterior of the needle defines the usual mechanism whereby additional liquid is introduced into the destination receptacle. For especially volume sensitive analyses this aspect of carryover is particularly troublesome.

In order to eliminate or minimize the effects of carryover it has been the practice to provide wash stations at convenient locations on the instrument. The wash station may include a well-like reservoir of a purging liquid, typically water, into which the needle is immersed. Alternatively or additionally, the purging liquid may be expelled through the needle while it is located at the wash station. The wash station may optionally be provided with an arrangement whereby a jet of drying air is forced under pressure through the needle or at the exterior surface thereof. In this manner the presence of residual material on the surface or the interior of the needle is removed. The needle is inserted into the wash station at any appropriate opportunity during the operation of the probe assembly.

Typical of analysis instruments having a wash station of the above form are those described in U.S. Pat. No. 3,964,526 (Sindermann), U.S. Pat. No. 4,318,885 (Suzuki et al.) and U.S. Pat. No. 3,552,212 (Ohlin). However, in these typical situations the wash station is fixed relative to the needle. Thus, the needle must be diverted to the wash station at each occasion when cleaning is required. Although the presence of a wash station is beneficial from the carryover aspect the requirement that the needle be physically relocated to the wash station detracts from the overall throughput of the instrument.

U.S. Pat. No. 4,323,537 (Mody) discloses an analysis system having a cleaning assembly in the form of a hollow collar movable with the needle. In this system, as the needle is raised and lowered it passes through the collar. However, full immersion of the needle into a well-like reservoir is precluded due to the structure of the collar. Such a collar structure, while sufficient to contain a low velocity jet of purging liquid expelled from the probe, is unable to contain a relatively high velocity liquid jet produced when the liquid pump is cycled at high rates. Therefore, the liquid pump must be slowed to limit the velocity of the purging liquid jet expelled from the probe. As a consequence the throughput of the instrument is slowed. Furthermore, a high velocity jet of purging liquid imparts a scrubbing action to the interior of the probe. This scrubbing action is lost when the velocity of the expelled liquid jet is slowed.

Accordingly, in view of the foregoing it is believed to be advantageous to provide a cleaning arrangement which utilizes an enclosed well-like reservoir operative to purge extraneous material from the interior and the exterior of the needle while at the same time not detract from the throughput of the instrument. It is also believed to be advantageous to provide a cleaning arrangement for a probe assembly which is mechanically able to contain a high velocity purging liquid jet, thus permitting the liquid pump to cycle at its maximum rate thereby allowing the maximum scrubbing action on the interior of the probe.

SUMMARY OF THE INVENTION

The present invention relates to a liquid dispensing apparatus for use in a chemical analysis instrument. The apparatus includes a support member preferably in the form of a cantilevered arm mounted for pivotal movement about a central vertical axis. As aspirating needle is mounted on the support member for movement with respect thereto. The needle is movable from a first location to a second location. In the preferred case the needle is operative at the first location to draw thereinto a predetermined volume of liquid and at the second location to dispense some portion of the aspirated liquid into a receptacle.

A cleaning assembly having a recess sized to receive the needle therein is movable with respect to the support member. In the preferred case the cleaning assembly is mounted to the needle for movement therewith. The cleaning assembly is movable with respect to the support member to a position proximal to the needle where the cleaning assembly may receive the needle to effect the cleaning of the same, thereby eliminating the necessity of the needle being moved to a predetermined stationary cleaning location after each dispensation of liquid.

The cleaning assembly includes a pair of arms each movable from an open to a closed disposition. In the closed disposition the arms are cooperable to define a well-like needle-receiving enclosed reservoir adapted to closely receive the needle and to permit the same to be immersed within the reservoir. The reservoir is connected to a low pressure region such that a cleaning liquid dispensed through the needle is drawn over the exterior surface of the needle to effect the cleaning of the interior and the exterior thereof.

The reservoir is defined by a pair of wellheads that are carried in an articulable manner on the ends of the arms of the cleaning assembly. One of the wellheads contains a planar flange while the other of the wellheads has a complementary cutout sized to receive the flange such that, when joined together, the wellheads cooperate to define an enclosed reservoir. The reservoir is structured so as to be mechanically able to withstand the force generated when a relatively high velocity jet of purging liquid is expelled from the needle.

BRIEF DESCRIPTION OF THE DRAWINGS

The invention will be more fully understood from the following detailed description thereof taken in connection with the accompanying drawings which form a part of this application and in which:

FIG. 2 is an enlarged side elevational view taken along view lines 2—2 of FIG. 1 illustrating the needle assembly and the mobile cleaning assembly, with the arms of the cleaning assembly being in the closed disposition;

FIG. 3 is a front elevational view of the needle assembly and cleaning assembly taken along view lines 3—3 of FIG. 2;

FIG. 4 is an enlarged plan view of the needle assembly taken along view lines 4—4 of FIG. 2;

FIG. 5 is a plan view of the cleaning assembly taken along view lines 5—5 in FIG. 2 showing the arms of the cleaning assembly in the open disposition;

FIG. 6 is an enlarged front view entirely in section, taken along section lines 6—6 of FIG. 5, showing the detailed construction of the wellheads of the cleaning assembly;

FIG. 7 is an enlarged isolated front sectional view of the wellheads shown in FIG. 6 with the wellheads being separated;

FIG. 8 is a section view of the wellheads taken along section lines 8—8 in FIG. 7;

FIG. 9 is an enlarged sectional view of the wellhead assembly of FIG. 6 illustrating the path of cleaning liquid within the chamber defined on the interior of the conjoined wellheads; and FIGS. 10A through 10D are a series of views illustrating the opening sequence of the arms of the cleaning assembly as the needle is moved with respect to the support member from the retracted position (FIG. 10A) through the intermediate position (FIGS. 10B, 10C) and toward the extended position (FIG. 10D).

DETAILED DESCRIPTION OF THE INVENTION

Figure 1:
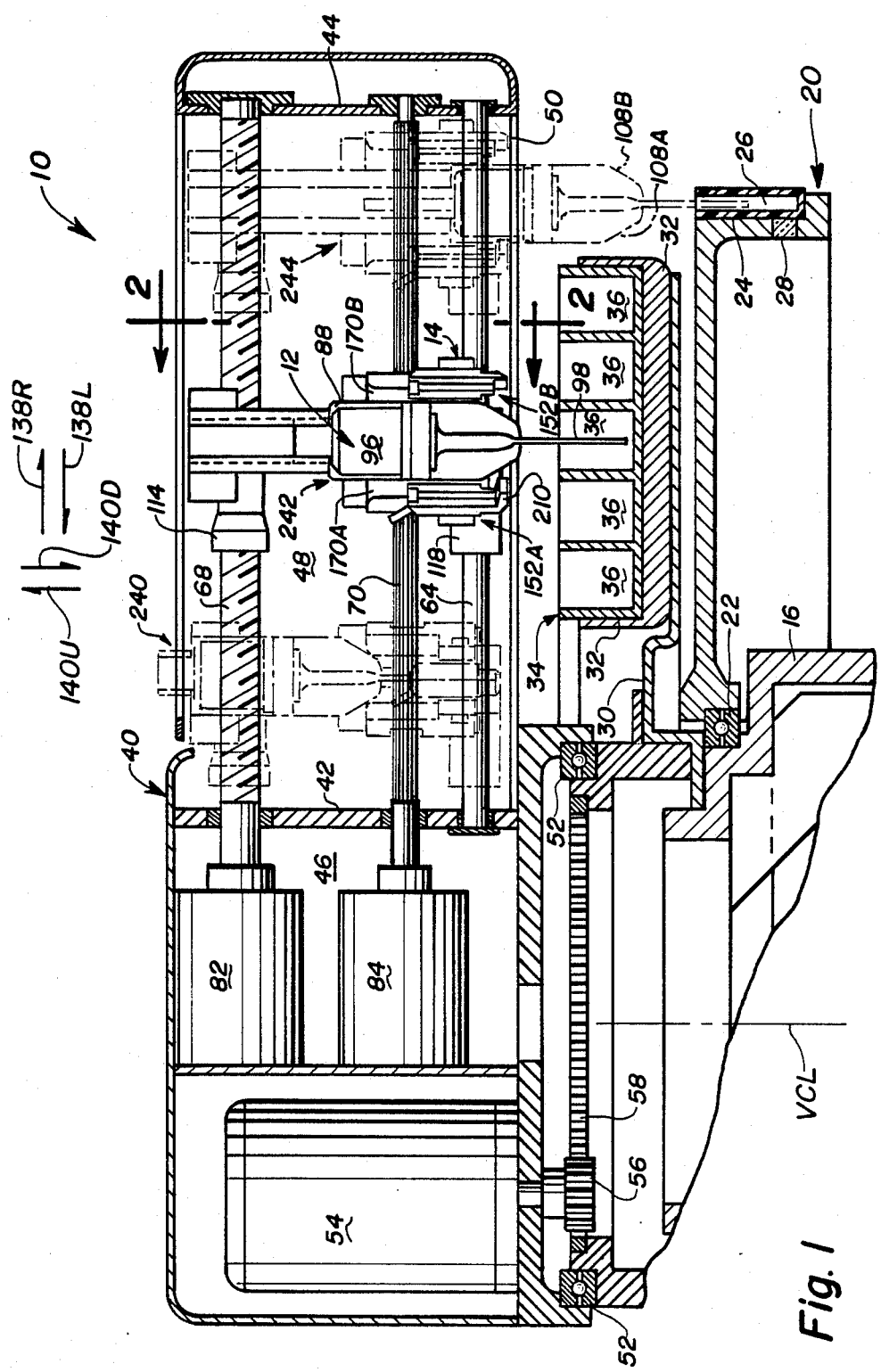
FIG. 1 is a side elevational view partially in section of a portion of a support member having an aspirating needle assembly mounted for movement with respect to the support member and having a mobile needle cleaning assembly in accordance with the present invention.

Throughout the following detailed description similar reference numerals refer to similar elements in all Figures of the drawings.

FIG. 1 is a side elevational view entirely in section of a portion of a chemical analysis instrument 10 having an aspirating needle assembly 12 and a mobile needle cleaning assembly 14 in accordance with the present invention. The cleaning assembly is operative to effect the cleaning of the aspirating needle assembly 12 without the necessity of relocating the needle assembly to a predetermined stationary cleaning location after each dispensation of liquid by the needle assembly 12. Moreover, the cleaning assembly includes structure operative to define an enclosed, closed bottom, well-like reservoir, or chamber, in which the needle may be received. The chamber is provided with a closed bottom which is mechanically able to withstand a relatively high velocity jet of cleansing and purging liquid being expelled from the interior of the needle.

The instrument 10 includes a support column 16 through which the central vertical axis VCL of the instrument 10 extends. A cuvette wheel 20 is mounted for rotational movement with respect to the support column 16 on a suitable bearing 22. The wheel 20 has an array of cavities 24 disposed on the periphery thereof. The cavities 24 are sized to received a sample receptacle, or cuvette, 26, such as a test tube or any similar sample carrying container. A radiation transparent window 28 is formed in the wheel 20 through which interrogating radiation may be introduced into and through the contents of the cuvette 26. The wheel 20 may be advanced in continuous or stepwise movements by any suitable drive arrangement, such as a stepper motor. A photometer (not shown) is suitably mounted for rotational movement about the vertical axis VCL whereby interrogating radiation may be directed toward the cuvette 26. Exemplary of an analysis instrument similar to that described and suitable for use with the present invention is that shown in application Ser. No. 642,814, filed Aug. 21, 1984 and assigned to the assignee of the present invention.

A reagent tray 30 is mounted on the support column 16. The tray 30 carries an insulating member 32 that receives a plurality of multi-compartmented disposable reagent vessels 34. Each vessel 34 has a plurality of reagent receiving cells 36 formed therein. The individual vessels 34 are supported on the upper surface of the tray 30 and emanate in a radial pattern with respect to the the axis VCL. The structure of the vessel 34 is disclosed in the copending application Ser. No. 757,576, assigned to the assignee of the present invention.

Mounted atop the support column 16 is a housing 40. The housing 40 is subdivided by an actuator support wall 42 and a bearing support wall 44 into an actuator chamber 46 and an needle traversing chamber 48. The housing 40 is open over at least its radially outer undersurface, as shown at 50, to permit the aspirating needle assembly 12 and the needle cleaning assembly 14 disposed in the traversing chamber 48 to project therefrom. The housing is also open over its upper surface. The housing 40 as an entire assembly is rotatable on a bearing 52 about the axis VCL by a drive motor 54. The shaft of the motor 54 carries a pinion gear 56 which engages a circular gear 58 mounted near to the top of the support column 16.

A guide shaft 64 is mounted between the walls 42 and 44. A traversing screw shaft 68 and an actuating gear shaft 70 extend in parallel to themselves and to the guide shaft 64 through the traversing chamber 48. Both the shafts 68 and 70 are rotationally mounted to the bearing support wall 44 and project in a support relationship through the actuator support wall 42. The inner end of the shaft 68 is connected to a suitable drive motor 82 which is mounted within the actuator chamber 46. The motor 82 serves as the motive source for the traversing action imparted to the aspirating needle assembly 12 in a manner to be discussed. Similarly, the inner end of the shaft 70 is connected to a motor 84 which serves as the motive source for the lifting or lowering action imparted to the aspirating needle assembly 12, as will also be discussed.

As may be seen from FIGS. 2, 3 and 4 the aspirating needle assembly 12 includes a baseplate 88 having outwardly flaring ears 92A and 92B thereon. A mounting band 94 projects from the baseplate 88 and receives an ultrasonic horn assembly 96. Suitable for use as the needle assembly 12 is the ultrasonic probe assembly disclosed and claimed in the copending application Ser. No. 757,574, also assigned to the assignee of the present invention.

The horn 96 has an elongated needle-like nozzle 98 with a central hollow passage 98P (FIG. 9) therein. A gear rack 100 is attached to the back of the baseplate 88 by screws 102. The lateral edges 106A and 106B of the baseplate 88 have cam surfaces 108A and 108B provided thereon for a purpose to be made clearer herein.

A carriage 110 has a substantially T-shaped channel 112 extending down the forward surface thereof. A radial drive nut 114 is attached by screws 116 (FIG. 2) to the rear of the carriage 110. The drive nut 114 accepts the drive shaft 68. The carriage 110 has a fitting 118 thereon through which the guide shaft 64 extends.

A bore 120 in the carriage 110 accepts the actuating bear shaft 70. An uper and a lower pinion 122A and 122B are respectively mounted within the carriage 110 on shafts 124A and 124B (FIG. 2). The ears 92 on the baseplate 88 of the needle assembly 12 are received within the channel 112 in the carriage 110 such that the gear rack 100 is mated in a driven interconnected relationship with the gear shaft 70 through the pinions 122A, 122B. The provision of the upper and lower gears 122A and 122B, respectively increases the stroke of travel of the plate 88. The sides of the carriage 110 are each provided with upper mounting abutments 126A, 126B and lower mounting abutments 128A, 128B. Bores 130A and 130B respectively extend in a registered fashion through the abutments 126A, 128A and 126B, 128B.

As may be understood from the description so far provided and from the drawings rotation of the screw shaft 68 causes the carriage 110 and the needle assembly 12 mounted thereon to traverse in reciprocal rectilinear directions as indicated by the arrows 138L and 138R. Through the interconnection between the rack 100 and the gear shaft 70, via the pinions 122A and 122B, rotation of the gear shaft 70 raises and lowers the needle assembly 12 in opposed rectilinear directions as indicated by the arrows 140U and 140D.

The needle cleaning assembly 14 in accordance with the present invention is, in the preferred embodiment, mounted to the needle carriage 110 for travel therewith and, thus, with the aspirating needle assembly 12. The cleaning assembly 14 includes a pair of arms 152A and 152B. The arms 152 are fabricated from a suitable material, such as an acetal resin material such as that sold by E. I. du Pont de Nemours and Company under the trademark "Delrin". Each arm 152A and 152B include a mounting shoulder 154A and 154B, respectively. Each shoulder 154A, 154B has a central bore 156A, 156B respectively extending therethrough. The appropriate bore 156 registers with the corresponding bores 130 provided in the mounting abutments 126, 128 on the carriage 110. Upper and lower enlarged counterbores 158 and 160 are provided in the shoulder 154 of each arm.

The main portions 166A, 166B of the arms 152A, 152B, respectively, extending forwardly of the shoulders 154 each carry a tapered cam surface 170A, 170B (FIG. 6). The forward end portions of the arms define mounting blocks 172A and 172B. The confronting surfaces 173A, 173B of the blocks 172A, 172B, respectively, are each bored, as at 174. A motion limiting stop member 178A, 178B (FIG. 5) is provided adjacent the inner confronting surfaces 173A, 173B, respectively, of the arms 152A, 152B, respectively, for a purpose to be described.

A pair of mating wellheads 184 and 186 are respectively mounted to the arms 152A and 152B through articulating ball and socket joints 188A and 188B, respectively. Each joint 188A, 188B includes a socket member 190A, 190B respectively mounted in a recess 192A, 192B respectively provided in the wellhead 184, 186. Each socket 190A, 190B respectively receives the ball head end of a ball shaft 194A, 194B. The end of the shafts 194A, 194B, opposite the ball end is provided with a fitting 196A, 196B respectively. The fittings 196A, 196B are respectively threadedly received into the bores 174A, 174B provided in the surfaces 173 of the mounting blocks 172 at the ends of the arms 152. Of course, it lies within the contemplation of the present invention that only one of the wellheads is provided with an articulating joint.

As seen in FIGS. 6, 7 and 8 the wellhead 184 is mounted to the left arm 152A, although it may be mounted to the other of the arms if desired. The wellhead 184 has a planar junction surface 202A with a central groove 204A formed therein. The groove 204A is intersected by an inclined channel 206A and a pair of inclined slots 208A and 208B. The lower end of the wellhead 184 has an sidewardly projecting flange 210 having a planar surface 212 thereon. A vacuum connection 214 extends into the wellhead 184 through an opening 216 and communicates with the groove 204A therein.

The wellhead 186 is mounted to the other arm 152B. This wellhead 186 is similarly provided with a conforming junction surface 202B having a central groove 204B therein. The groove 204B is intersected by an inclined channel 206B and a corresponding pair of slots 208C and 208D. The lower end of the wellhead 186 is provided with a cutout 218. The cutout 218 is contoured to accept the end of the flange 210 extending from the wellhead 184.

The wellheads 184, 186 accept in their respective recesses 192A, 192B the socket portions 190A, 190B of the joints 188A, 188B respectively. By virtue of the joints 188A, 188B each of the wellheads 184, 186 is respectively mounted for articulating movement with respect to its respective associated arm 152A, 152B. Thus, when the arms 152A, 152B are displaced toward each other in a manner to be explained the confronting junction surfaces 202 are brought into closely abutting engagement one with the other. Any misalignment or deviations from parallelism between the planar junction surfaces 202A, 202B are accommodated by the articulation of the wellheads 184, 186 on the joints 188. The three dimensional articulating motion of the wellheads is limited either by the stop members 178A, 178B or by the confronting surfaces 173A, 173B on the arms 152A, 152B, respectively (FIG. 5).

When the wellheads 184, 186 are in the closed disposition a chamber 220 is defined on the interior of the conjoined wellheads by the cooperative registration of the central grooves 204A, 204B. The chamber 220 is closed at its lower boundary by the planar surface 212 of the flange 210 carried on the wellhead 184. The chamber 220 so formed is thus substantially well-like in configuration, that is, bounded on all sides by the material of the wellheads 184, 186 and closed on the bottom of the planar surface 212 of the flange 210. The chamber 220 communicates with the ambient air via the channels 206A and 206B as well as by a pair of channels defined by the registration of the inclined slot 208A with the slot 208C and the slot 208B with the slot 208D. In addition, the chamber 220 communicates with a source of low pressure via the vacuum connection 214 received in the opening 216. The wellheads 184, 186 are each fabricated from a conductive material and are connected, as shown in FIG. 10, so as to form part of an electrical circuit 221 operative to provide an indication 222 when the wellheads 184, 186 are conjoined to define the chamber 220.

The arms 152 are each mounted for pivotal movement with respect to the carriage 110. To facilitate this mounting a pivot rod 232A, 232B (FIGS. 3, 4 and 5) is introduced through the bores 156A, 156B provided in each shoulder 154A, 154B and the bores 130A, 130B extending through the mounting abutments 126A, 126B and 128A, 128B. A wound spring 236A, 236B, 236C and 236D is received in each of the counterbores 158A, 158B, 160A and 160B provided in the shoulders 154A, 154B of the arms 152A, 152B, respectively. One end of each of the wound springs 236 acts against the respective shoulder 154 in which the spring 236 is disposed while the other end of the spring acts against the carriage 110. A typical arrangement is shown in FIG. 5 where the springs 236A and 236B respectively act against the arms 154A and 154B and the respective sides of the carriage 110. The springs 236 thus serve to bias the arms 152 into the closed disposition shown in FIGS. 2, 3 and 5.

The operation of the device shown in the figures may be understood by reference to FIG. 1 taken in connection with FIGS. 10A through 10D. The needle assembly 12 initially occupies a retracted position with respect to the support housing 40, as shown in FIG. 10A and at the region indicated by reference character 240 in FIG. 1. In the retracted position the lower end of the needle 98 lies above the vessel 34 such that transition of the needle assembly 12 and the cleaning assembly 14 mounted therewith in the directions of the arrows 138L and 138R may be effected without the needle 98 striking against the vesel 34. The needle assembly 12 may be translated in the directions 138L or 138R by energization of the actuator 82 connected to the screw shaft 68. This causes the shaft 68 to rotate in the appropriate direction and to displace the assembly 12 along the guide shaft 64 in the selected direction. The needle assembly 12 is thus positionable along the guide shaft 64 to occupy any predetermined axial location therealong. For example, the needle assembly 12, while still in the retracted position, may be positioned above any one of the receptacles 36 defined in the vessel 34 or may be located above the cuvette 26 carried on the periphery of the wheel 20.

When the assembly 12 has reached the appropriate location along the shaft 64 the needle assembly 12 may be raised or lowered in the directions 140U or 140D by the rotation of the gear shaft 70. The teeth of the shaft 70 engage the teeth in the rack 100 (through the pinions 122) to cause the end of the needle 98 to be lifted or lowered dependent upon the direction of rotation of the shaft 70. In a typical instance the needle 98 is axially positioned at a predetermined position over one of the receptacle 36, lowered into the receptacle to aspirate a predetermined measure of liquid as shown at 242 in FIG. 1, raised to the transport position as shown at 240 in FIG. 1, displaced axially to the periphery of the wheel 20 above one of the cuvettes 26, and lowered into the cuvette 26, as shown at 244 in FIG. 1, where dispensation of the previously aspirated liquid may occur. Of course, the needle 98 may simply be positioned over a cuvette of interest and a liquid pumped through the needle 98 and into the cuvette 26.

The cleaning assembly 14 mounted for movement with the needle assembly 12 is movable from the closed to the open dispositions and thus out of the way of the vertical movements of the needle assembly 12. As the needle assembly 12 is lowered in the direction 140D by the gear shaft 70 the inclined cam surfaces 108 on the lower end of the mounting plate 88 are brought into contact with the inclined cam surfaces 170 on the arms 152. This action, in response to the motion of the needle, has the effect of urging the arms 152 in the directions of the arrows 248 from the closed toward the open dispositions. When the cam surfaces 108 have been lowered below the surfaces 170 on the arms 152 the side edges 106 of the mounting plate 88 serve to hold the arms 152 in the open disposition against the force of the bias springs 236.

Once the arms 152 are opened the needle 98 may be lowered to whatever extent may be permitted or accommodated by the structure of the instrument. Thus, for example, were the needle assembly positioned in the location shown in FIG. 1 by the numeral 242 the receptacle 36 would limit motion of the needle 98 while at reference numeral 244 further motion of the actuation gear shaft 70 on the lowering direction would cause the needle 98 to project into the cuvette 26. The point to note is that the arms 152 of the cleaning assembly are movable from their closed to their open dispositions (FIGS. 10A and 10B, 10C respectively) to permit the unhampered vertical motion of the needle assembly 12 to occur.

The cleaning assembly 14 is operative to effect the thorough cleaning of the needle 98 without the necessity of displacing the needle to a predetermined fixed cleaning position. As the needle is withdrawn in the upward direction 140U from the fully extended position (FIG. 10D) or from the intermediate (FIG. 10B) vertical position, the cam surfaces 108 of the mounting plate 88 are again presented to the cam surfaces 170 on the arms 152. The arms 152 begin to close due to the action of the biasing springs 236. The cams 108, 170 maintain a gradual closing action of the arms 152.

As the arms 152 close the wellheads 184, 186 converge upon the lower end of the needle 98 to surround the same. Any deviations from parallelism between the surfaces 202 on the wellheads are accomodated by slight articulation of the wellheads 184, 186 with respect to the associated arms 152A, 152B through the articulating joints, as discussed. The flange 210 provided on the wellhead 184 extends into and is received by the cutout 218 provided in the other of the wellheads 186 to enclose the bottom of the chamber 220. With the needle 98 received in the chamber 220 a suction is drawn via the connection 214. Simultaneously, a purging liquid may be caused to flow through the needle 98. As the purging liquid exits the mouth of the passage 98P (FIG. 10) of the needle 98 it is directed downwardly in the chamber 220 where it strikes against the planar surface 212 of the flange 210 defining the lower boundary of the chamber 220.

The purging liquid is deflected by through essentially one hundred eighty degrees in two ninety degree increments by the action of the flange 210 and the walls of the grooves 204. Since the chamber is in fluid communication with a pressure less than atmospheric pressure (via the connection 214) air is drawn into the chamber 220 through the channels 206A, 206B, and the channels defined by the registration of the slots 208A-208D. The purging liquid, deflected by the planar surface 212 of the flange 210 and the surface of the groove, is thus caused to flow upwardly over the exterior surface of the needle 98 to the connection 214 as air is drawn into the chamber 220. It should be noted that in the preferred case the planar surface 212 of the flange 210 lies substantially perpendicular to the sidewalls of the groove 202 in the wellhead 184. Thus, the liquid expelled from the mouth of the needle 98 is deflected through two right angle turns, as discussed. It lies within the contemplation of the present invention, however, that the planar surface 212 of the flane 210 may define other than a ninety degree angle with respect to the wall of the groove and remain within the contemplation of the present invention.

As may be readily appreciated the cleaning assembly in accordance with the present invention is adapted to enhance the throughput of the instrument by eliminating the necessity of displacing the needle assembly to a predetermined fixed cleaning location. Since the cleaning assembly is freely movable with respect to the housing, indeed since in the preferred case it moves with the needle, the movement of the needle to the cleaning station is avoided, since the cleaning station in effect moves to the needle. It should be appreciated, of course, that the cleaning assembly need not be mounted directly on the needle, as is shown in the preferred embodiment. Any arrangement whereby the cleaning assembly is movably mounted with respect to the needle so the necessity of displacing the needle to a fixed cleaning station is avoided lies within the contemplation of the present invention.

In addition, in view of the foregoing those skilled in the art may readily appreciate that with the structure in accordance with the present invention the cleaning arrangement 14 is, in effect, provided with a movable, enclosed, well-like reservoir-type cleaning chamber. That is, the chamber defined by the cooperative association of the conjoined wellheads exhibits a closed lower boundary. Such a structure is mechanically able to withstand the forces exerted by a cleansing liquid as the same is expelled from the end of the needle 98 while minimizing the possibility of leaking. As a result the liquid dispensing pump of the instrument need not be operated at a pumping pressure lower than its standard pumping pressure, as would be required with a cleaning arrangement having a collar with an open bottom. Since no reduction in pump pressure is necessary the turbulent cleaning action imparted to the interior of the needle by a relatively high speed jet of purging liquid is still maintained, thus enhancing the cleaning of the needle.

The ability of the cleaning arrangement to move with the aspirating needle, coupled with the ability of the closed bottom chamber to mechanically withstand the pressure exerted by the expelled purging liquid, permits thorough cleaning of the needle while ehancing the throughput of the instrument.

Those skilled in the art, having the benefit of the teachings of the present invention as hereinabove set forth may effect numerous modifications thereto. It should be understood that these and other modifications lie within the scope of the present invention as set forth in the appended claims.

What is claimed is:

1. A liquid dispensing apparatus comprising:
   a support member;
   a dispensing needle translatable with respect to the support member from a first to a second position; and
   a cleaning assembly mounted to the dispensing needle for movement therewith with respect to the support member, the cleaning assembly having an enclosed, well-like needle receiving chamber having a closed bottom for receiving the needle therein.

2. A liquid dispensing apparatus comprising:
   a support member;
   a dispensing needle vertically translatable with respect to the support member from a first to a second position;
   a cleaning assembly mounted for movement with respect to the support member, the cleaning assembly having a pair of arms each being movable from a first to a second disposition, in the first position the the arms of cleaning assembly being cooperable to define an enclosed, well-like needle receiving chamber having a closed bottom, the chamber receiving the needle therein, while in the second disposition the cleaning assembly being spaced from the needle to permit the needle to vertically displace with respect to the support; and
   an actuator responsive to the movement of the needle to displace the cleaning assembly from the first to the second position.

3. A liquid dispensing apparatus comprising:
   a support member;
   a dispensing needle translatable with respect to the support member from a first to a second position, the needle being operative at the second position to dispense a predetermined measure of liquid into a receptacle;
   a cleaning assembly mounted for movement with respect to the support member, the cleaning assembly having a pair of arms each being movable from an open to a closed disposition, in the closed disposition the arms being cooperable to define an enclosed, well-like needle receiving chamber having a closed bottom, the chamber being adapted to receive the needle therein; and
   an actuator responsive to the movement of the needle to displace the arms from the open to the clsoed disposition.

4. The liquid dispensing apparatus of claim 3 wherein each arm has a wellhead thereon, each of the wellheads having a groove therein, one of the wellheads having a flange and the other of the wellheads having a corresponding cutout formed therein, when the arms are in the closed disposition the flange in the one wellhead is received in the cutout in the other wellhead and the grooves in the wellheads register with each other to form the well-like needle receiving chamber having the closed bottom.

5. The liquid dispensing apparatus of claim 4 wherein at least one of the wellheads is connected to the arm with which it is associated by an articulating joint.

6. A liquid dispensing apparatus for transferring a liquid stored at a first location to a receptacle disposed at a second spaced location, comprising:
   a support member;
   a dispensing needle rectilinearly translatable in a first direction with respect to the support member from the first to the second location, the needle being operative at the first location to draw thereinto a predetermined volume of liquid and at the second location to dispense a predetermined portion of the liquid into the receptacle, the needle also being movable with respect to the support member in a second direction perpendicular to the first direction from an initial, retracted, position to a final, extended, position;

a cleaning assembly having a pair of arms each being movable from an open to a closed disposition, in the closed disposition the arms being cooperable to define an enclosed, well-like needle receiving chamber having a closed bottom, the chamber receiving the needle therein when the needle occupies the retracted position; and an actuator mounted to the needle and engageable with the arms for displacing the same from the open to the closed disposition as the needle moves from the retracted to the extended position.

7. The liquid dispensing apparatus of claim 6 wherein each arm has a wellhead at an outer end thereof, each wellhead having a junction surface with a groove therein, one of the wellheads having a flange and the other of the wellheads having a corresponding cutout formed therein, when the arms are in the close disposition the flange in the one wellhead is received into the cutout in the other wellhead and the grooves in the wellheads register with each other to form the well-like needle receiving chamber having the closed bottom.

8. The liquid dispensing apparatus of claim 7 wherein one of the wellheads has an opening therein whereby the chamber may be exposed to a pressure lower than atmospheric pressure.

9. The liquid dispensing apparatus of claim 8 wherein at least one channel extends through one of the wellheads and into fluid communication with the chamber whereby air may be drawn into the chamber when the chamber is exposed to a pressure lower than atmospheric pressure.

10. The liquid dispensing apparatus of claim 8 wherein each of the wellheads has at least one channel extending therethrough into fluid communication with the chamber whereby air may be drawn into the chamber when the chamber is exposed to a pressure lower than atmospheric pressure.

11. The liquid dispensing apparatus of claim 10 further comprising an articulating joint for connecting one of the wellheads to the arm with which it is associated.

12. The liquid dispensing apparatus of claim 8 further comprising an articulating joint for connecting one of the wellheads to the arm with which it is associated.

13. The liquid dispensing apparatus of claim 7 further comprising an articulating joint for connecting one of the wellheads to the arm with which it is associated.

14. The liquid dispensing apparatus of claim 10 wherein the flange has a planar surface thereon, the planar surface being perpendicular to the junction surface of the wellhead.

15. The liquid dispensing apparatus of claim 8 wherein the flange has a planar surface thereon, the planar surface being perpendicular to the junction surface of the wellhead.

16. The liquid dispensing apparatus of claim 7 wherein the flange has a planar surface thereon, the planar surface being perpendicular to the junction surface of the wellhead.

17. The liquid dispensing apparatus of claim 15 wherein the needle is mounted on a plate having a cam surface thereon and the arms are each provided with a corresponding cam surface, the actuator being operative upon displacement of the needle plate to dispose the cam surface on the plate into cooperative engagement with the cams on the arms to displace the arms from the closed to the open disposition.

18. The liquid dispensing apparatus of claim 14 wherein the needle is mounted on a plate having a cam surface thereon and the arms are each provided with a corresponding cam surface, the actuator being operative upon displacement of the needle plate to dispose the cam surface on the plate into cooperative engagement with the cams on the arms to displace the arms from the closed to the open disposition.

19. The liquid dispensing apparatus of claim 11 wherein the needle is mounted on a plate having a cam surface thereon and the arms are each provided with a corresponding cam surface, the actuator being operative upon displacement of the needle plate to dispose the cam surface on the plate into cooperative engagement with the cams on the arms to displace the arms from the closed to the open disposition.

20. The liquid dispensing apparatus of claim 7 wherein the needle is mounted on a plate having a cam surface thereon and the arms are each provided with a corresponding cam surface, the actuator being operative upon displacement of the needle plate to dispose the cam surface on the plate into cooperative engagement with the cams on the arms to displace the arms from the closed to the open disposition.

21. The liquid dispensing apparatus of claim 8 wherein the needle is mounted on a plate having a cam surface thereon and the arms are each provided with a corresponding cam surface, the actuator being operative upon displacement of the needle plate to dispose the cam surface on the plate into cooperative engagement with the cams on the arms to displace the arms from the closed to the open disposition.

22. The liquid dispensing apparatus of claim 21 wherein the sides of the plate are configured to define holding surfaces for holding the arms in the open disposition.

23. The dispensing apparatus of claim 20 wherein the sides of the plate are configured to define holding surfaces for holding the arms in the open disposition.

24. The dispensing apparatus of claim 19 wherein the sides of the plate are configured to define holding surfaces for holding the arms in the open disposition.

25. The dispensing apparatus of claim 18 wherein the sides of the plate are configured to define holding surfaces for holding the arms in the open disposition.

26. The dispensing apparatus of claim 17 wherein the sides of the plate are configured to define holding surfaces for holding the arms in the open disposition.

27. The liquid dispensing apparatus of claim 13 further comprising a motion limiting stop surface on the arm having the articulating joint for limiting the articulating motion of that wellhead.

28. The liquid dispensing apparatus of claim 12 further comprising a motion limiting stop surface on the arm having the articulating joint for limiting the articulating motion of that wellhead.

29. The liquid dispensing apparatus of claim 11 further comprising a motion limiting stop surface on the arm having the articulating joint for limiting the articulating motion of that wellhead.

* * * * *